United States Patent

Holderbaum et al.

Patent Number: 5,821,380
Date of Patent: Oct. 13, 1998

[54] 2-CYANOACRYLIC ESTERS

[75] Inventors: Martin Holderbaum, Ludwigshafen; Alexander Aumüller, Neustadt; Hubert Trauth, Dudenhofen; Guido Voit, Schriesheim; Karin Sperling, Neustadt; Alfred Krause, Speyer, all of Germany

[73] Assignee: BASF Aktiengesellschaft, Ludwigshafen, Germany

[21] Appl. No.: 836,042

[22] PCT Filed: Nov. 3, 1995

[86] PCT No.: PCT/EP95/04312

§ 371 Date: May 12, 1997

§ 102(e) Date: May 12, 1997

[87] PCT Pub. No.: WO96/15102

PCT Pub. Date: May 23, 1996

[30] Foreign Application Priority Data

Nov. 10, 1994 [DE] Germany .......................... 44 40 055.1
May 31, 1995 [DE] Germany .......................... 195 19 895.6

[51] Int. Cl.$^6$ .............................. C07C 255/07; A61K 7/42
[52] U.S. Cl. ........................ 558/443; 558/400; 558/402; 524/397; 524/396; 524/186; 514/535; 514/536; 512/22; 424/59; 424/60; 424/400; 424/401; 252/401; 252/403; 252/405
[58] Field of Search ..................................... 558/443, 402, 558/400; 524/397, 186, 396; 252/401, 403, 405; 424/59, 60, 400, 401; 512/22; 514/535, 536

[56] References Cited

U.S. PATENT DOCUMENTS 3,215,725  11/1965  Strobel et al. .

FOREIGN PATENT DOCUMENTS

A1 381 743   3/1965  France .
41 22 475    7/1991  Germany .
WO 94/15907  7/1994  WIPO .

OTHER PUBLICATIONS

Organikum Organisch–Chemisches Grundpraktikum, 15$^{th}$ Edition, 1977.
Polymer Science U.S.S.R., vol. 15. No. 5, May 1974.
Chemical Abstracts, vol. 79, No. 21, Nov. 26, 1973.
Patent Abstracts of Japan, vol. 13, No. 494 (C–651), 8 Nov. 1989.
Patent Abstracts of Japan, vol. 9, No. 287 (C–314), 14 Nov. 1985.
Patent Abstracts of Japan, vol. 9, No. 267 (C–310) 24 Oct. 1985.
Patent Abstracts of Japan, vol. 8, No. 122 (C–227), 8 Jun. 1984.

Primary Examiner—Johann Richter
Assistant Examiner—Ebenezer O. Sackey
Attorney, Agent, or Firm—Oblon, Spivak, McClelland, Maier & Neustadt, P.C.

[57] ABSTRACT

Novel 2-cyanoacrylic esters I

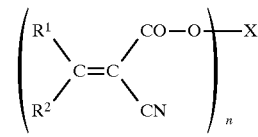

where the radicals have the following meanings:

$R^1$ and $R^2$ are each hydrogen or a radical having an iso- or heterocyclic ring system with at least one iso- or heteroaromatic nucleus, and at least one of the radicals $R^1$ or $R^2$ must be different from hydrogen, n is from 2 to 10, and X is, when n=2, a radical of the formula II

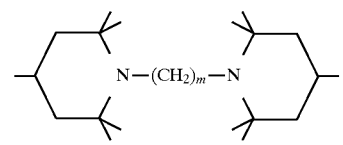

where m is from 2 to 8, and X is, when n>2, the radical of an n-hydric aliphatic or cycloaliphatic polyol having 3–20 carbon atoms, it also being possible for a cycloaliphatic radical to contain 1 or 2 hetero atoms, and for an aliphatic radical to be interrupted by up to 8 non-adjacent oxygen atoms, sulfur atoms, imino or $C_1$–$C_4$-alkylimino groups, are used as light stabilizers.

20 Claims, No Drawings

2-CYANOACRYLIC ESTERS

This application is a 371 of PCT/EP95/04312 filed Nov. 3, 1995.

BACKGROUND OF THE INVENTION

1. Field of the Invention

The present invention relates to novel 2-cyanoacrylic esters of the formula I

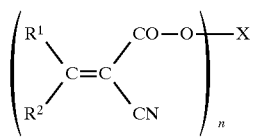

where $R^1$ and $R^2$ are each hydrogen or a radical having an iso- or heterocyclic ring system with at least one iso- or heteroaromatic nucleus, and at least one of the radicals $R^1$ or $R^2$ must be different from hydrogen, n is from 2 to 10, and X is, when n=2, a radical of the formula II

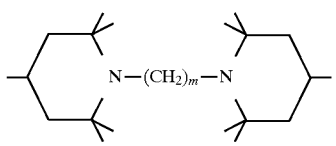

where m is from 2 to 8, and

X is, when n>2, the radical of an n-hydric aliphatic or cycloaliphatic polyol having 3–20 carbon atoms, it also being possible for a cycloaliphatic radical to contain 1 or 2 hetero atoms, and for an aliphatic radical to be interrupted by up to 8 non-adjacent oxygen atoms, sulfur atoms, imino or $C_1$–$C_4$-alkylimino groups.

The invention furthermore relates to a process for preparing the compounds I, to the use thereof as stabilizers, in particular against the action of light, for organic materials, in particular for cosmetic or dermatological preparations, plastics or paints, and to organic materials which contain the compounds I.

2. Description of the Background

U.S. Pat. No. 3,215,725 and DE-A 41 22 475 disclose 2-cyanoacrylic esters of monohydric and dihydric alcohols as light stabilizers for plastics and paints.

However, these compounds have the technical disadvantage of a relatively high volatility. Since, moreover, they are only conditionally compatible with many organic materials, especially with polyolefins, they are prone, especially on storage at elevated temperature, to migrate and consequently display exudation.

SUMMARY OF THE INVENTION

It is an object of the present invention to remedy these disadvantages by novel stabilizers of the 2-cyanoacrylic ester type.

We have found that this object is achieved by the 2-cyanoacrylic esters of the general formula I defined at the outset.

We have furthermore found a process for preparing these compounds, their use as light protection factors or stabilizers for organic materials, and organic formulations which contain these compounds as stabilizers.

DETAILED DESCRIPTION OF THE INVENTION

If the radicals $R^1$ and $R^2$ are different, the 2-cyanoacrylic ester groups of I may be either in the cis or the trans form.

The preparation of the compounds usually results in mixtures of these isomers. It is possible to separate these isomers, but this is unnecessary for most industrial applications.

Suitable organic radicals for $R^1$ and $R^2$ are, in general, cyclic structures which contain at least one iso- or heteroaromatic nucleus, which is preferably linked directly to the 3-C atom of the acrylic group but can also be linked to this carbon atom via aliphatic or cycloaliphatic groups and via a linker —$NR^3$—.

$R^1$ or $R^2$ is preferably a radical of the formula III

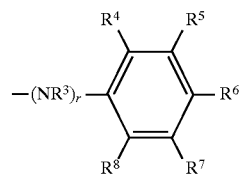

where $R^3$ is hydrogen or $C_1$–$C_{10}$-alkyl, r is 0 or 1, and $R^4$ to $R^8$ are each, independently of one another, hydrogen, $C_1$–$C_8$-alkyl, chlorine, bromine, cyano, nitro, amino, mono($C_1$–$C_4$-alkyl)amino, di($C_1$–$C_4$-alkyl)amino, hydroxyl, $C_1$–$C_8$-acyl, $C_1$–$C_8$-acyloxy, $C_1$–$C_{18}$-alkoxy, $C_1$–$C_{12}$-alkoxycarbonyl, $C_3$–$C_6$-cycloalkyl or $C_3$–$C_6$-cycloalkoxycarbonyl.

Suitable radicals $R^3$ besides hydrogen are $C_1$–$C_{10}$-alkyl radicals such as methyl, ethyl, n-propyl, isopropyl, isopropyl [sic], n-propyl [sic], n-butyl, isobutyl, sec-butyl, tert-butyl, n-pentyl, isopentyl, sec-pentyl, tert-pentyl, neopentyl, n-hexyl, n-heptyl, n-octyl, isooctyl, 2-ethylhexyl, n-nonyl, isononyl, n-decyl and isodecyl.

If one or more of the radicals $R^4$ to $R^8$ are $C_1$–$C_8$-alkyl, $C_1$–$C_8$-acyl, $C_1$–$C_{18}$-alkoxy or $C_1$–$C_{12}$-alkoxycarbonyl, the alkyl radicals therein can be, for example, methyl, ethyl, n-propyl, isopropyl, n-propyl [sic], n-butyl, isobutyl, sec-butyl, tert-butyl, n-pentyl, isopentyl, sec-pentyl, tert-pentyl, neopentyl, n-hexyl, n-heptyl, n-octyl or 2-ethylhexyl.

Examples of suitable longer-chain alkyl radicals in $C_1$–$C_{18}$-alkoxy and $C_1$–$C_{12}$-alkoxycarbonyl groups are nonyl, 2-methylnonyl, isononyl, 2-methyloctyl, decyl, isodecyl, 2-methylnonyl [sic], undecyl, isoundecyl, dodecyl, isododecyl, tridecyl, isotridecyl, tetradecyl, pentadecyl, hexadecyl, heptadecyl and octadecyl. (The terms isooctyl, isononyl, isodecyl and isotridecyl are trivial names derived from the carbonyl compounds obtained by the oxo synthesis; compare in this connection Ullmann's Encyclopedia of Industrial Chemistry, 5th edition, Vol. A1, pages 290–293, and Vol. A10, pages 284 and 285).

Examples of suitable $C_3$–$C_6$-cycloalkyl radicals are cyclopropyl, cyclobutyl, cyclopentyl, methylcyclopentyl or cyclohexyl. These cycloalkyl groups are also suitable radicals in $C_3$–$C_6$-cycloalkylcarbonyl groups.

Preferred 2-cyanoacrylic esters I are those where $R^3$ is hydrogen, methyl or ethyl.

Further preferred 2-cyanoacrylic esters I are those where up to three, particularly preferably one, of the radicals $R^4$ to $R^8$ are hydrogen, $C_1$–$C_4$-alkyl, chlorine, cyano, hydroxyl, acetyl, $C_1$–$C_5$-alkoxy, $C_1$–$C_8$-alkoxycarbonyl or cyclohexoxycarbonyl, and the remainder of these radicals are hydrogen.

Particularly preferred 2-cyanoacrylic esters I are those where $R^6$ is hydroxyl, methoxy, ethoxy, propoxy, isopropoxy, butoxy, isobutoxy, sec-butoxy or tert-butoxy, because such 4-substituted phenyl groups contribute to the stabilizing effect of the compounds. For the same reason, 2-cyanoacrylic esters where $R^5$ and/or $R^7$ are hydrogen, methyl or tert-butyl, in particular when $R^6$ is hydroxyl, are also particularly preferred.

Preferred compounds I according to the invention are those where r is 0.

Further preferred compounds according to the invention are those where $R^1$ or $R^2$ is hydrogen, those where $R^1$ and $R^2$ are identical radicals, and those where one of the radicals $R^1$ or $R^2$ is phenylamino, p-tolylamino, p-methoxy- or p-ethoxycarbonylphenylamino and the other is hydrogen.

Another preferred radical for $R^1$ or $R^2$ is the chroman residue Ib

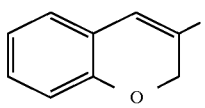

Ib or its substituted derivates, because these also enhance the stabilizing effect of the compounds I.

Further suitable radicals $R^1$ and $R^2$ are heterocyclic groups such as substituted or unsubstituted thiophenyl [sic], furfuryl and pyridyl radicals.

If n=2, X is a radical of the formula II

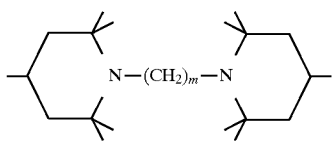

II where m is from 2 to 8, preferably 2 to 6, but particularly preferably 2.

If n>2, X is the radical of an n-hydric aliphatic or cycloaliphatic alcohol. These alcohols may be linear or branched, and their carbon chains can be interrupted by one or more oxygen or sulfur atoms, by imino groups (—NH—) or $C_1$–$C_4$-alkylimino groups.

The group X is preferably derived from the folowing known polyols:

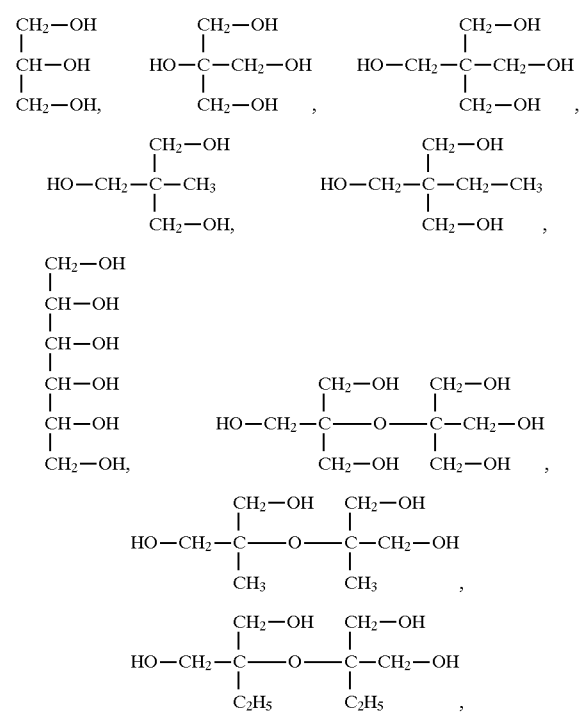

-continued

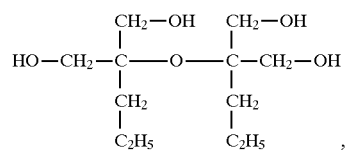

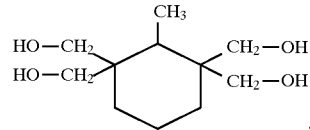

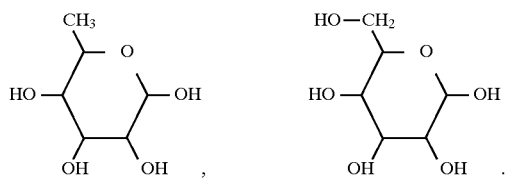

The 2-cyanoacrylic esters of the formula I where $R^1$ and $R^2$ are not linked via a nitrogen atom to the β-C atom are preferably obtainable by reacting cyanoacetic esters of the formula III

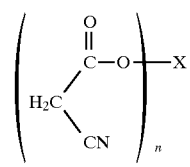

III with n mol of a compound (IV)

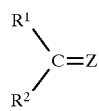

IV under the conditions of the Knoevenagel condensation. The reaction can, for example, be carried out in aromatic solvents such as toluene or xylene (see, for example, Organikum, 1976 edition, page 572). However, polar organic solvents such as dimethylformamide, dimethylacetamide, N-methylpyrrolidone, trialkyl orthoformate or alcohols such as n-propanol, n-butanol, ethylene glycol, diethylene glycol, ethylene glycol monomethyl ether, cyclohexanol or similar compounds are preferably used. If the starting compounds themselves form a liquid mixture, it is possible to dispense with an additional solvent. The reaction is preferably carried out at from 20° to 180° C., particularly preferably from 40° to 150° C. The pressure is preferably atmospheric pressure. The use of a catalyst or catalyst mixture may be advantageous depending on the reactivity of the compound IV employed. Examples of suitable catalysts are ammonium acetate, piperidine and β-alanine and acetates thereof.

Catalysts which can additionally be used for the reaction if the reaction times are very long are Lewis acids such as $AlCl_3$, $ZrCl_4$, $TiCl_4$ or, in particular, $ZnCl_2$ in the amounts customary for this purpose.

The 2-cyanoacrylic esters of the formula I where r is 1, ie. where one radical $R^1$ or $R^2$ is linked via a nitrogen atom to the β-C atom, can advantageously be prepared by reacting a cyanoacetic ester of the formula IV

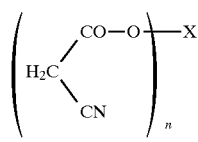

with an aromatic amine of the formula Va

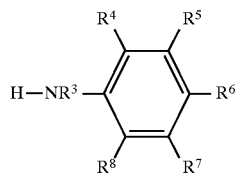

in the presence of trialkyl orthoformate. Examples of trialkyl orthoformates which have proven suitable are trimethyl orthoformate and triethyl orthoformate.

The cyanoacetic esters II can be prepared, for example, by reacting cyanoacetic acid or esters thereof with the appropriate polyols $X(OH)_n$ in the presence of a catalyst such as boric acid, $Na_2CO_3$ or $K_2CO_3$ or tetrabutyl orthotitanate, preferably in toluene or xylene.

The compounds according to the invention are outstandingly suitable for stabilizing organic materials against the action of light, oxygen and heat.

Examples of plastics which can be stabilized by the compounds I according to the invention are:

polymers of mono- and diolefins, eg. low and high density polyethylene, polypropylene, linear poly-1-butene, polyisoprene, polybutadiene, and copolymers of mono- or diolefins or mixtures of said polymers;

copolymers of mono- or diolefins with other vinyl monomers, eg. ethylene/alkyl acrylate copolymers, ethylene/alkyl methacrylate copolymers, ethylene/vinyl acetate copolymers or ethylene/acrylic acid copolymers;

polystyrene and copolymers of styrene or α-methylstyrene with dienes and/or acrylic derivatives, eg. styrene/butadiene, styrene/acrylonitrile (SAN), styrene/ethyl methacrylate, styrene/butadiene/ethyl acrylate, styrene/acrylonitrile/methacrylate, acrylonitrile/butadiene/styrene (ABS) or methyl methacrylate/butadiene/styrene (MBS);

halogenated polymers, eg. polyvinyl chloride, polyvinyl fluoride, polyvinylidene fluoride and copolymers thereof;

polymers derived from α,β unsaturated acids and derivatives thereof, such as polyacrylates, polymethacrylates, polyacrylamides and polyacrylonitriles;

polymers derived from unsaturated alcohols and amines or their acrylic derivatives or acetals, eg. polyvinyl alcohol and polyvinyl acetate;

polyurethanes, polyamides, polyureas, polyphenylene ethers, polyesters, polycarbonates, polyoxymethylenes, polysulfones, polyether sulfones and polyether ketones.

It is furthermore possible to use the compounds I according to the invention to stabilize surface coatings, eg. industrial coatings. Among these, particular attention is drawn to stoved coatings, and among these in turn to automotive coatings, preferably two-layer coatings.

The compounds I according to the invention can be added in solid or dissolved form to the coating material. Their good solubility in coating systems is a particular advantage in this context.

The compounds I according to the invention are preferably used for stabilizing polyolefins, especially polyethylene, polycarbonates, polyamides, polyesters, polystyrene, ABS and polyurethanes. It is also possible, in particular, to stabilize sheets of said plastics.

For these applications, the compounds are employed in concentrations of from 0.01 to 5% of the weight of the plastic, preferably in a concentration of from 0.02 to 2% by weight. Combination with other stabilizers, for example antioxidants, metal deactivators or other light stabilizers, and with antistatic agents or flame retardants, is often advantageous. Examples of particularly important costabilizers are sterically hindered phenols, and phosphites, phosphonites, amines and sulfur compounds.

Examples of suitable costabilizers are:

phenolic antioxidants such as 2,6-di-tert-butyl-4-methylphenol, n-octadecyl β-(3,5-di-tert-butyl-4-hydroxyphenol)propionate [sic], 1,1,3-tris(2-methyl-4-hydroxy-5-tert-butylphenyl)butane, 1,3,5-trimethyl-2,4,6-tris(3,5-di-tert-butyl-4-hydroxybenzyl)-benzene, 1,3,5-tris(3,5-di-tert-butyl-4-hydroxybenzyl) isocyanurate, 1,3,5-tris[β-(3,5-di-tert-butyl-4-hydroxyphenyl)propionylethyl]isocyanurate, 1,3,5-tris(2,6-dimethyl-3-hydroxy-4-tert-butylbenzyl) isocyanurate and pentaerythritol tetrakis[β-(3,5-di-tert-butyl-4-hydroxy)propionate] [sic], phosphorous-containing antioxidants such as tris (nonylphenyl)phosphite, distearyl pentaerythritol phosphite [sic], tris(2,4-di-tert-butylphenyl)phosphite, tris (2-tert-butyl-4-methylphenyl)phosphite, bis(2,4-di-tert-butylphenyl)pentaerythritol diphosphite and tetrakis(2,4-di-tert-butylphenyl)4,4'-biphenylene diphosphite, sulfur-containing antioxidants such as dilauryl thiodipropionate, dimyristyl thiodipropionate, distearyl thiodipropionate, pentaerythritol tetrakis(β-laurylthiopropionate) and pentaerythritol tetrakis(β-hexylthiopropionate), sterically hindered amines such as bis(2,2,6,6-tetramethylpiperidyl)sebacate, bis(1,2,2,6,6-pentamethylpiperidyl)sebacate, bis(1,2,2,6,6-pentamethylpiperidyl)esters, N,N'-bis(formyl)-bis(2,2,6,6-tetramethyl-4-piperidyl)-1,6-hexanediamine, the condensate of 1-hydroxy-2,2,6,6-tetramethyl-4-hydroxypiperidine and succinic acid, the condensate of N,N'-(2,2,6,6-tetramethylpiperidyl) hexamethylenediamine and 4-tert-octylamino-2,6-dichloro-1,3,5-s-triazine, poly[3-(eicosyl/tetracosyl)-1-(2,2,6,6-tetramethyl-4-piperidinyl)-2,5-pyrrolidinedione], tris(2,2,6,6-tetramethylpiperidyl) nitrilotriacetate, tetrakis(2,2,6,6-tetramethyl-4-piperidyl)-1,2,3,4-butanetetracarboxylic acid [sic], 1,1'-(1,2-ethanediyl)bis(3,3,5,5-tetramethylpiperazinone), the condensates of 4-amino-2,2,6,6-tetramethylpiperidines and tetramethylolacetylenediureas, and 2-(2'-hydroxyphenyl)benzotriazoles, 2-hydroxybenzophenones, aryl esters of hydroxybenzoic acids, α-cyanocinnamic acid derivatives, nickel compounds or oxanilides.

The compounds I according to the invention can be mixed, in particular with plastics, using all known apparatus and methods for mixing stabilizers or other additives into polymers.

The 2-cyanoacrylic esters I according to the invention are distinguished by high compatibility with conventional types of plastic and by good solubility and excellent compatibility in conventional coating systems. As a rule, they have very little or no intrinsic color, are stable and nonvolatile at conventional plastic- and surface coating-processing temperatures and afford long-lasting protection to the materials treated with them. Above all, however, they show virtually no tendency to migrate in plastics.

UV radiation is divided into three regions: the UV-A region (320–400 nm), the UV-B region (290–320 nm) and the UV-C region (200–290 nm). The high-energy UV-C region is predominantly absorbed by the ozone layer. Radiation in the UV-B region is responsible in particular for the development of sunburn and skin cancer. UV-A radiation produces on lengthy exposure tanning of the skin but is also partly responsible for aging of the skin.

Because of the favorable solubility properties and the good absorption properties, especially in the UV-A region, the compounds according to the invention are particularly suitable for applications in cosmetics and dermatological products. The compounds can also be used advantageously for protecting cosmetic products such as perfumes, creams and lotions. Combinations with sunscreen agents which absorb in the UV-B region are particularly preferred. The 2-cyanoacrylic esters I are used for cosmetic formulations in concentrations of from 0.05 to 15%, preferably from 0.1 to 10%, of the total weight of the cosmetic formulation.

Other organic materials to which the compounds according to the invention can advantageously be added are pharmaceutical formulations such as pills and suppositories, photographic recording materials, especially photographic emulsions, and precursors for plastics and paints.

EXAMPLES

Preparation Examples

Example 1

16.2 g (0.04 mol) of 2,2-bis(hydroxymethyl)-1,3-propanediol tetracyanoacetate were dissolved in 100 ml of N,N-dimethylformamide (DMF) and heated to 80° C. To this were added dropwise under a gentle stream of nitrogen 29.6 g (0.16 mol) of benzophenone imine (97% pure) dissolved in 25 ml of DMF, over the course of 2 h. The mixture was heated at about 100° C. until ammonia evolution ceased. It was then cooled and 300 ml of ethanol were added. The product was initially oily and became solid after lengthy stirring. It was filtered off with suction and washed with ethanol.

37.5 g (88.4%) of theory of the compound of the formula

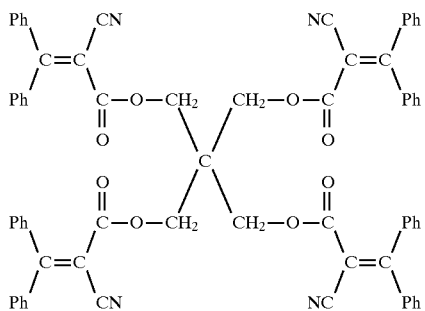

were obtained with melting point 123°–126° C. (glassy); UV $(CH_2Cl_2)$: $\lambda_{max}$=310 nm, $\epsilon$=50,000.

Example 2

The compound of the formula

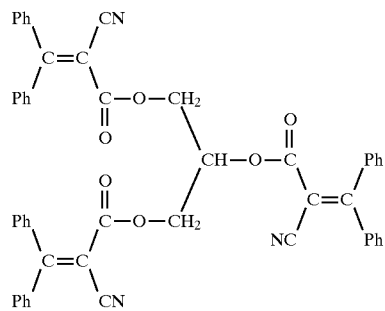

was prepared in a similar way to Example 1 from the appropriate cyanoacetic ester and benzophenone imine; melting point: 100°–104° C.; UV $(CH_2Cl_2)$: $\lambda_{max}$=310 nm, $\epsilon$=36,400.

Example 3

The compound of the formula

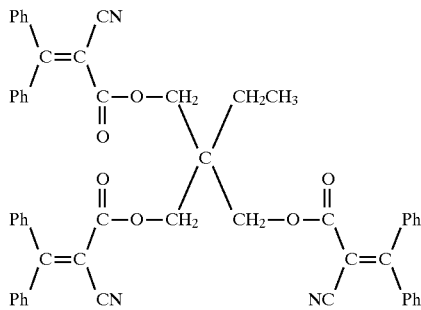

was prepared in a similar way to Example 1 from the appropriate cyano [sic] ester and benzophenone imine; melting point: 92° C.; UV $(CH_2Cl_2)$: $\lambda_{max}$=308 nm, $\epsilon$=36,700.

Example 4

The compound of the formula

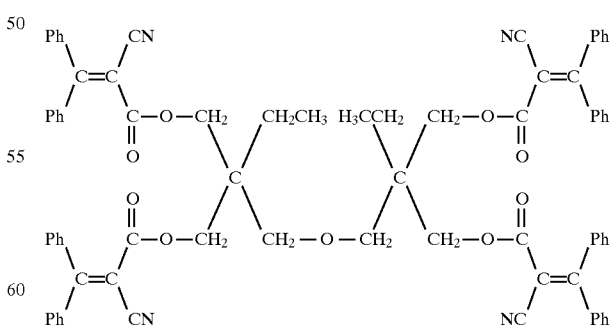

was prepared in a similar way to Example 1 from the appropriate cyanoacetic ester and benzophenone imine; melting point: 83°–95° C.; UV $(CH_2Cl_2)$: $\lambda_{max}$=308 nm, $\epsilon$=51,700.

Example 5

The compound of the formula

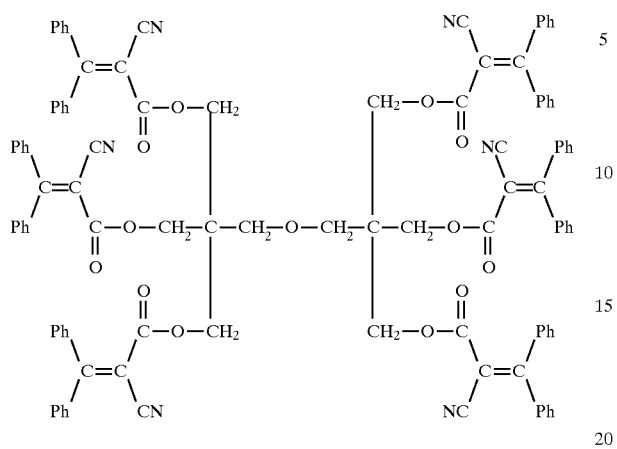

was prepared in a similar way to Example 1 from the appropriate cyanoacetic ester and benzophenone imine; melting point 124°–128° C.; UV (CH$_2$Cl$_2$): $\lambda_{max}$=308 nm, $\epsilon$=76,000.

Example 6

30.3 g (0.075 mol) of 2,2-bis(hydroxymethyl)-1,3-propanediol tetracyanoacetate were refluxed with 29.8 g (0.32 mol) of aniline and 52 g (0.35 mol) of trimethyl orthoformate for 6 h. Then 80 ml of ethanol were added, and the suspension was refluxed for 1 h.

It was then filtered while hot under suction and the residue was thoroughly washed with ethanol.

55 g (90% of theory) of a yellowish compound of the formula

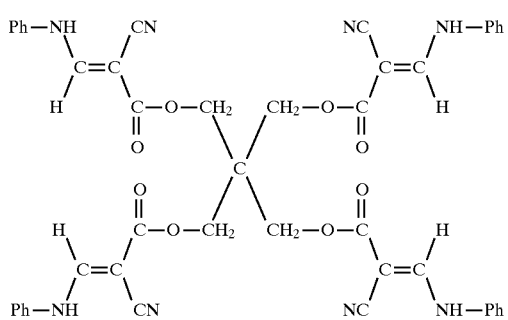

were obtained with melting point 298°–300° C.; UV (DMSO): $\lambda_{max}$=322 nm, $\epsilon$=98,000 (DMSO=dimethyl sulfoxide).

Examples 7 and 8

The compound of the formula

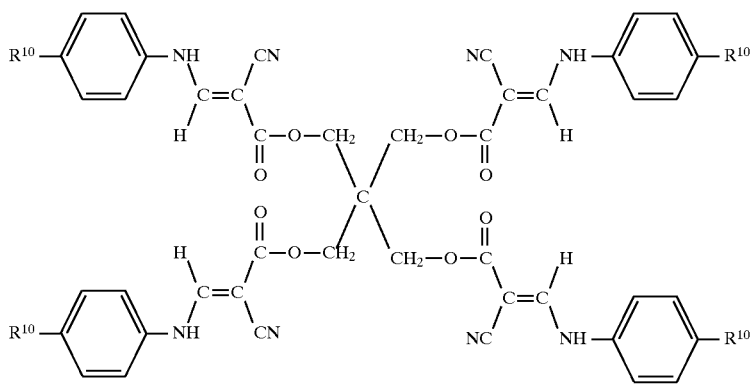

$R^{10}$=CH$_3$ (Example 7) or COOCH$_2$CH$_3$ (Example 8) were [sic] prepared in a similar way to Example 6 from the appropriate cyanoacetic ester, the appropriate aromatic amine and trimethyl orthoformate; melting points: 321°–323° C. (Example 7) and 269°–273° C. (Example 8); UV (DMSO): $\lambda_{max}$=326 nm (Example 7) and 334 nm (Example 8), $\epsilon$=99,000 (Example 7) and 150,000 (Example 8).

Example 9
The compound of the formula

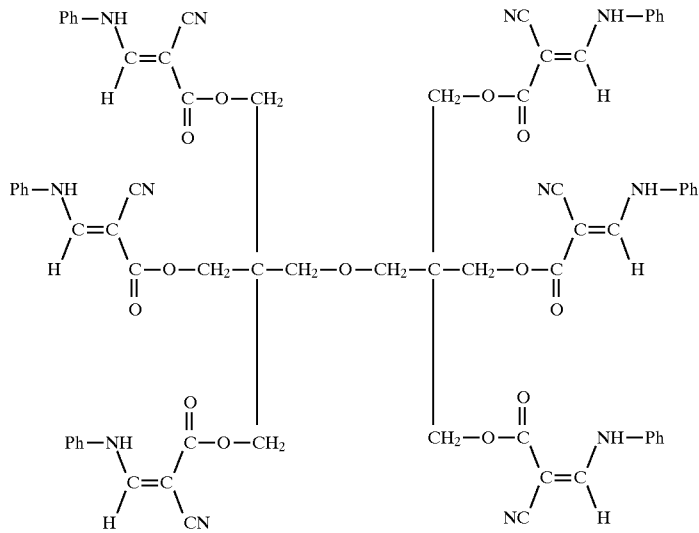

was prepared in a similar way to Example 6 from the appropriate cyanoacetic ester, aniline and trimethyl orthoformate; melting point 240°–248° C.; UV (CH$_2$Cl$_2$): $\lambda_{max}$= 320 nm; $\epsilon$=145,000.

Examples 10–36

General preparation method for the reaction of cyanoacetic esters IV with aldehydes ($R^1$ or $R^2$=hydrogen)

0.1 mol of an n-functional cyanoacetic ester IV,

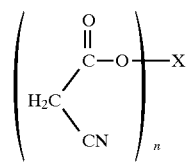 IV which has been obtained by reacting cyanoacetic acid with the appropriate n-hydric alcohol in a conventional way, were [sic] reacted with 0.12 n mol of an aldehyde Vb $$R^1 \atop R^2 \!\!\diagup\!\! C=O \qquad Vb$$

in 100 ml of N,N-dimethylacetammide [sic] in the presence of 0.5 ml of piperidine and 0.3 ml of glacial acetic acid. After 3 hours at 70° C., the precipitate was separated off, washed with methanol and water and dried.

Details of these experiments and the properties of the compounds I obtained are to be found in the following table.

| No. | X | $R^1$ or $R^2$ | *γmax [nm] | Molar extinction coefficient ε [1.cm$^{-1}$.mol$^{-1}$] | Melting point [°C.] | Yield [%] |
|---|---|---|---|---|---|---|
| 10 |  | H$_3$CO—C$_6$H$_4$— | 342 | 57000 | >265 | 95 |

-continued
| No. | X | R¹ or R² | *γmax [nm] | Molar extinction coefficient ε [l.cm⁻¹.mol⁻¹] | Melting point [°C.] | Yield [%] |
|---|---|---|---|---|---|---|
| 11 | 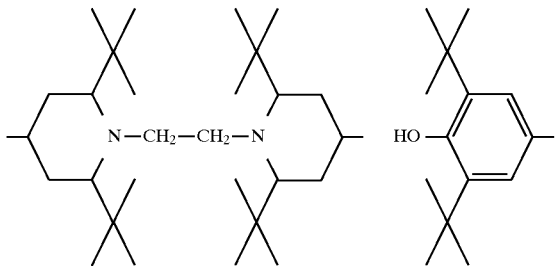 | 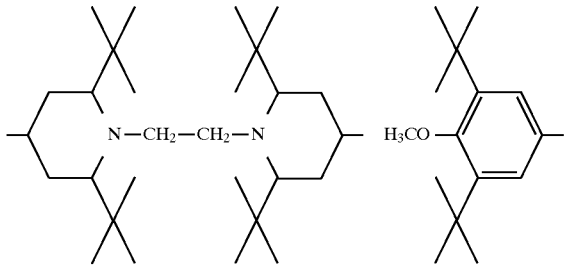 | 350 | 59000 | >265 | 70 |
| 12 | 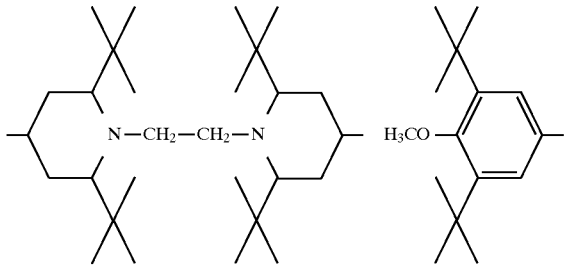 | 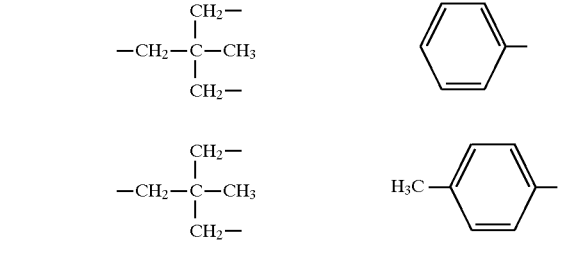 | 336 | 47000 | >265 | 92 |
| 13 | 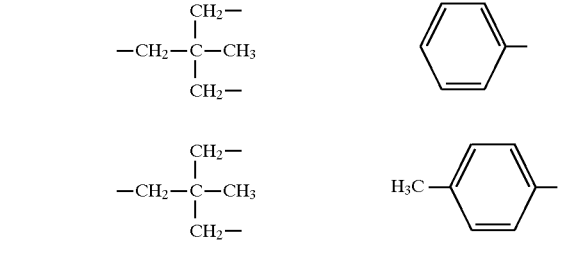 | 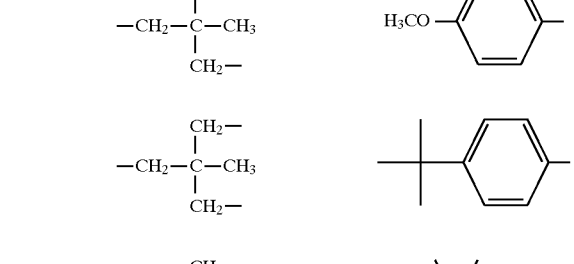 | 306 | 59188 | 110–112 | 70 |
| 14 | 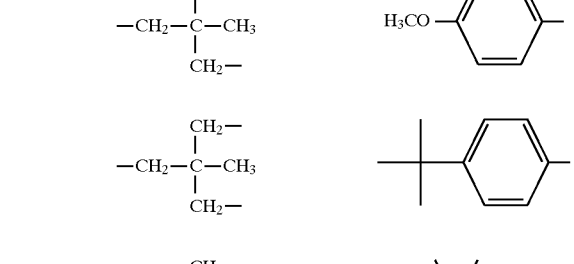 | 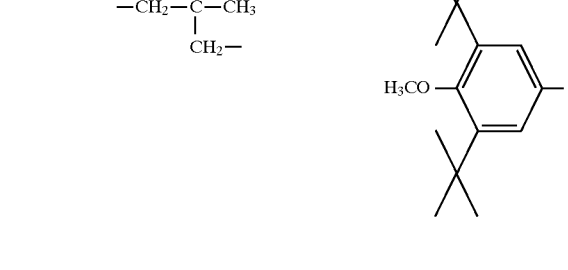 | 322 | 66678 | 115–120 | 77 |
| 15 | 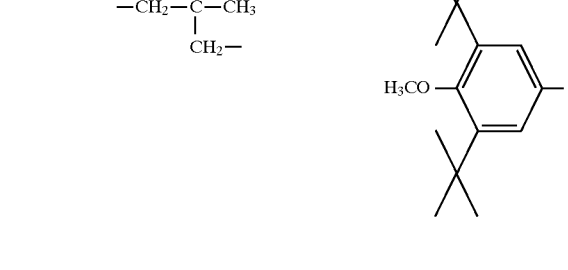 |  | 346 | 76912 | 75–80 | 90 |
| 16 |  | | 324 | 73332 | 90–95 | 84 |
| 17 | | | 340 | 72000 | 179–181 | 70 |

-continued
| No. | X | R[1] or R[2] | *γmax [nm] | Molar extinction coefficient ε [1.cm⁻¹.mol⁻¹] | Melting point [°C.] | Yield [%] |
|---|---|---|---|---|---|---|
| 18 | 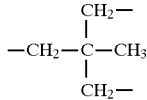 | 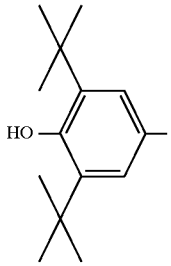 | 353 | 72000 | 170–174 | 77 |
| 19 | 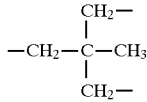 | 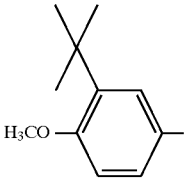 | 354 | 72100 | 95–100 | 88 |
| 20 | 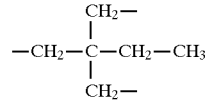 | 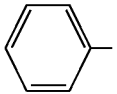 | 306 | 58256 | 114–116 | 63 |
| 21 | 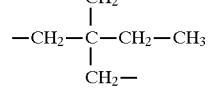 | 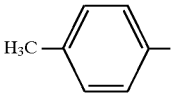 | 322 | 67090 | 95–102 | 74 |
| 22 | 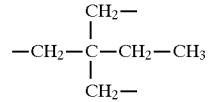 | 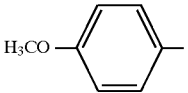 | 346 | 75519 | 30–35 | 73 |
| 23 | 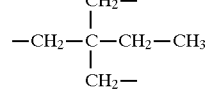 | 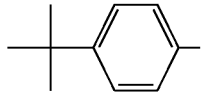 | 322 | 57601 | 168–170 | 67 |
| 24 | 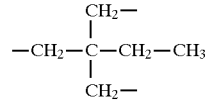 | 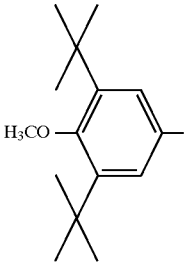 | 338 | 68000 | 103–105 | 74 |
| 25 | 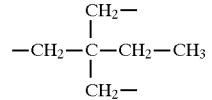 | 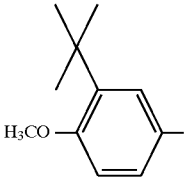 | 354 | 72000 | 85–87 | 74 |

-continued

| No. | X | R¹ or R² | *γmax [nm] | Molar extinction coefficient ε [l.cm⁻¹.mol⁻¹] | Melting point [°C.] | Yield [%] |
|---|---|---|---|---|---|---|
| 26 | —CH₂—C(CH₂—)(CH₂—)—CH₂— | 3,5-di-tert-butyl-4-hydroxyphenyl | 358 | 106480 | 275–276 | 66 |
| 27 | —CH₂—C(CH₂—)(CH₂—)—CH₂— | 4-H₃CO-phenyl | 346 | 102298 | 215–216 | 90 |
| 28 | —CH₂—C(CH₂—)(CH₂—)—CH₂— | phenyl | 308 | 63909 | 148–155 | 79 |
| 29 | —CH₂—C(CH₂—)(CH₂—)—CH₂— | 4-H₃C-phenyl | 324 | 102273 | 250 | 79 |
| 30 | —CH₂—C(CH₂—)(CH₂—)—CH₂— | 4-tert-butyl-phenyl | 324 | 101131 | 130–131 | 67 |
| 31 | —CH₂—C(CH₂—)(CH₂—)—CH₂— | 3,5-di-tert-butyl-4-methoxyphenyl | 342 | 51000 | 98–100 | 60 |
| 32 | —CH₂—C(CH₂—)(CH₂—)—CH₂— | 3-tert-butyl-4-methoxyphenyl | 356 | 110500 | 115–118 | 87 |
| 33 | —CH₂—C(CH₂—)(CH₂—)—CH₂—O—CH₂—C(CH₂—)(CH₂—)—CH₂— | 4-H₃C-phenyl | 320 | 120582 | 128–132 | 65 |
| 34 | —CH₂—C(CH₂—)(CH₂—)—CH₂—O—CH₂—C(CH₂—)(CH₂—)—CH₂— | 4-H₃CO-phenyl | 342 | 145000 | 105–108 | 88 |

-continued

| No. | X | R¹ or R² | *γmax [nm] | Molar extinction coefficient ε [1.cm⁻¹.mol⁻¹] | Melting point [°C.] | Yield [%] |
|---|---|---|---|---|---|---|
| 35 | −CH₂−C(CH₂−)(CH₂−)−CH₂−O−CH₂−C(CH₂−)(CH₂−)−CH₂− | (3,5-di-tert-butyl-4-methoxyphenyl) | 338 | 149300 | 150–151 | 58 |
| 36 | −CH₂−C(CH₂−)(CH₂−)−CH₂−O−CH₂−C(CH₂−)(CH₂−)−CH₂− | (3-tert-butyl-4-methoxyphenyl) | 352 | 145000 | 135–140 | 51 |

*UV measurements in $CH_2Cl_2$

Example 37

Use Example: Migration test in polyethylene 0.3% by weight of the UV stabilizer indicated below was dissolved in polyethylene by extrusion twice at a polymer temperature of 180° C., and then the polymer was granulated and blown to films 100 μm thick.

After storage at room temperature (20° C.) or in an oven (50° C.) for ten days, the surface of the film was assessed visually according to the following criteria:

| | |
|---|---|
| + | no deposit |
| o | slight deposit |
| − | heavy deposit |

The following table shows the UV stabilizers used and the results of the tests:

| UV stabilizer | Storage at 20° C. | Storage at 50° C. |
|---|---|---|
| Compound from Example No. 1 | + | + |
| Compound A (for comparison) | o | − |
| Compound B (for comparison) | − | − |

A: 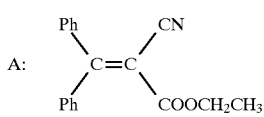

B (disclosed in (1)): 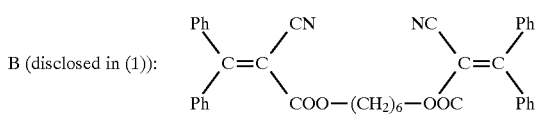

We claim:

1. A 2-cyanoacrylic ester of the formula (I):

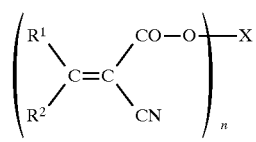

wherein one of $R^1$ or $R^2$ is hydrogen and the other is a radical of the formula (III):

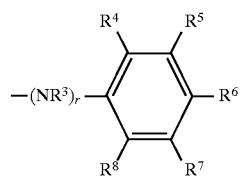

wherein $R^3$ is hydrogen or $C_1$–$C_{10}$-alkyl; r is 0 or 1; and $R^4$ to $R^8$ are each, independently of one another, hydrogen, $C_1$–$C_8$-alkyl, chlorine, bromine, cyano, nitro, amino, mono-($C_1$–$C_4$-alkyl)amino, di($C_1$–$C_4$-alkyl)amino, hydroxyl, $C_1$–$C_8$-acyl, $C_1$–$C_8$-acyloxy, $C_1$–$C_{18}$-alkoxy, $C_1$–$C_{12}$-alkoxycarbonyl, $C_3$–$C_6$-cycloalkyl or $C_3$–$C_6$-cycloalkoxycarbonyl;

n is from 2 to 10; and

X is, when n is 2, a radical of the formula (II):

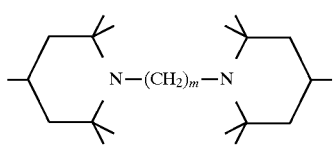

wherein m is from 2 to 8; and

X is, when n>2, a radical of an n-hydric aliphatic cycloaliphatic polyol having 3 to 20 carbon atoms, said cycloaliphatic radical optionally containing one or two heteroatoms, and said n-hydric aliphatic radical optionally being interrupted by up to eight non-adjacent oxygen atoms, sulfur atoms, imino or $C_1$–$C_4$-alkylimino groups.

2. The 2-cyanoacrylic ester of claim 1, wherein $R^3$ is hydrogen, methyl or ethyl.

3. The 2-cyanoacrylic ester of claim 1, wherein up to three of the radicals $R^4$ to $R^8$ are each independently hydrogen, $C_1$–$C_4$-alkyl, chlorine, cyano, hydroxyl, acetyl, $C_1$–$C_4$-alkoxy, $C_1$–$C_8$-alkoxycarbonyl or cyclohexoxycarbonyl, and the remainder of these radicals being hydrogen.

4. The 2-cyanoacrylic ester of claim 1, wherein $R^6$ is a hydroxyl group or $C_1$–$C_4$-alkoxy group.

5. The 2-cyanoacrylic ester of claim 1, wherein $R^5$ or $R^7$ or both are each independently hydrogen, methyl or tert-butyl.

6. The 2-cyanoacrylic ester of claim 1, wherein r is 0.

7. The 2-cyanoacrylic ester of claim 1, wherein X is the radical of an n-hydric polyol having 3 to 12 carbon atoms, which may be interrupted in its linear or branched carbon skeleton by up to 3 non-adjacent oxygen atoms, and n is from 3 to 6.

8. A process for preparing the 2-cyanoacrylic ester of claim 1, where r is 0, which comprises:

reacting a cyanoacetic ester of the formula (IV):

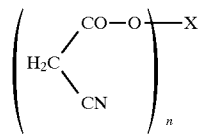

with n mol of a compound of the formula (V):

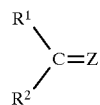

where Z is oxygen or NH, under conditions of a Knoevenagel condensation in a polar solvent and optionally in the presence of a catalyst.

9. The process of claim 8, wherein said polar solvent is selected from the group consisting of dimethylformamide, dimethylacetamide, N-methylpyrrolidone, trialkyl orthoformate, n-propanol, n-butanol, ethylene glycol, diethylene glycol, ethylene glycol monomethyl ether and cyclohexanol.

10. The process of claim 8, which is effected at a temperature of from about 20° to 180° C.

11. The process of claim 10, which is effected at a temperature of from about 40° to 150° C.

12. The process of claim 8, which is effected in the presence of a catalyst selected from the group consisting of ammonium acetate, piperidine, β-alanine, piperidine acetate, β-alanine acetate, $AlCl_3$, $ZrCl_4$, $ZnCl_2$, and $TiCl_4$.

13. A process for preparing 2-cyanoacrylic esters as claimed in claim 1, where r is 1, which comprises:

reacting a cyanoacetic ester of the formula (IV):

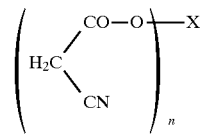

with an aromatic amine of the formula (Va):

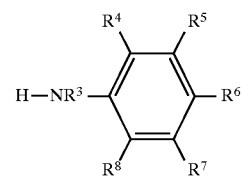

in the presence of trialkyl orthoformate.

14. The process of claim 13, wherein said trialkyl orthoformate is selected from the group consisting of trimethyl orthoformate and triethyl orthoformate.

15. An organic material stabilized against the action of light, oxygen and heat, which comprises from 0.01 to 10% by weight, based on the amount of organic material, of one or more 2-cyanoacrylic esters of claim 1.

16. A cosmetic or dermatological preparation stabilized against the action of light, oxygen and heat, which comprises from 0.01 to 15% by weight, based on the amount of this preparation of one or more 2-cyanoacrylic esters of claim 1.

17. A plastic or paint stabilized against the action of light, oxygen and heat, which comprises from 0.01 to 10% by weight, based on the amount of the plastic or paint, of one or more 2-cyanoacrylic esters of claim 1.

18. A method of stabilizing an organic material, comprising combining an effective amount of the 2-cyanoacrylic ester of claim 1, with at least one organic material.

19. A method of stabilizing a cosmetic or dermatological composition, comprising combining an effective amount of a 2-cyanoacrylic ester of claim 1, with a cosmetic or dermatological composition.

20. A method of stabilizing a plastic or paint, comprising combining an effective amount of the 2-cyanoacrylic ester of claim 1, with at least one plastic or paint.

* * * * *